(12) United States Patent
Dumoulin et al.

(10) Patent No.: US 6,584,337 B2
(45) Date of Patent: Jun. 24, 2003

(54) METHOD AND SYSTEM FOR EXTENDED VOLUME IMAGING USING MRI

(75) Inventors: Charles Lucian Dumoulin, Ballston Lake, NY (US); Yudong Zhu, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/683,124

(22) Filed: Nov. 21, 2001

(65) Prior Publication Data

US 2003/0100825 A1 May 29, 2003

(51) Int. Cl.⁷ .............................................. A61B 5/055
(52) U.S. Cl. ...................... 600/410; 600/415; 324/309
(58) Field of Search ................... 600/415, 410, 600/419; 324/306, 309, 307

(56) References Cited

U.S. PATENT DOCUMENTS

| 4,825,162 A | 4/1989 | Roemer et al. ............. 324/318 |
| 5,167,232 A | 12/1992 | Parker et al. ............. 128/653.3 |
| 5,423,315 A | 6/1995 | Margosian et al. ....... 128/653.2 |
| 5,910,728 A | 6/1999 | Sodickson ................... 324/309 |
| 6,037,771 A | 3/2000 | Liu et al. ..................... 324/309 |
| 6,223,065 B1 * | 4/2001 | Misic et al. ................ 600/410 |
| 6,230,040 B1 * | 5/2001 | Wang et al. ................ 600/415 |

* cited by examiner

*Primary Examiner*—Ruth S. Smith
(74) *Attorney, Agent, or Firm*—Jean K. Testa; Patrick K. Patnode

(57) ABSTRACT

A method and apparatus for producing an image from an extended volume of interest using a Magnetic Resonance Imaging (MRI) system are provided. The apparatus comprises a magnet assembly, a gradient coil assembly, at least one radiofrequency coil, a positioning device for translating the volume using along an axis of the MRI system and a plurality of receivers. A plurality of MR signals are detected from the radiofrequency (RF) coil, as the positioning device is translated, and are sent to the plurality of receivers. Each of the receivers are configured to be adjusted in either phase or frequency in response to the positioning device being translated. A plurality of respective sub-images are computed corresponding to the plurality of MR signals for each of the receivers and for the given field-of-view (FOV) at each of the incremented positions. A composite image of the volume of interest is formed by combining the respective sub-images.

12 Claims, 2 Drawing Sheets

METHOD AND SYSTEM FOR EXTENDED VOLUME IMAGING USING MRI

BACKGROUND OF INVENTION

This invention relates to a method and system for medical imaging. More particularly, this invention relates to a method and system for extended volume imaging using a Magnetic Resonance Imaging (MRI) system and employing a moving patient table.

Certain clinical situations require that a head-to-toe scan of a patient be made. For example, metastatic cancer can occur anywhere in the body and patients at risk for metastatic disease need to be evaluated regularly. Currently head-to-toe or, alternatively, extended volume imaging is generally performed with whole body positron emission tomography (PET) systems or nuclear studies in which small amounts of radioactive substances are given to the patient and allowed to collect in regions of rapid tumor growth. The imaging sensitivity and specificity of magnetic resonance (MR), however, makes MR a more desirable choice for diagnosis particularly when Gadolinium (Gd) contrast agents are employed. Gd contrast agents are typically administered intravenously and tend to collect in regions of angiogenesis associated with active tumors. Unfortunately, MR scanners have limited sensitive volumes and whole body scanning requires that a series of images be made at different stations. Patient motion and table registration can make the joining of these separate images a challenge and tend to create image artifacts referred to as "stitching artifacts".

Generally, imaging using a MRI system involves imaging a volume of interest in a MRI scanner's usable volume. The usable volume is defined as a contiguous area inside the patient bore of a Magnetic Resonance scanner and it can be limited in size. Typically, when the usable volume fails to cover an extended object, a method for examining the whole volume containing the object employs repeated executions of positioning and imaging a fraction of the whole volume within the scanner's usable volume to obtain regional images. A subsequent assembling operation then assembles or "stitches" the regional images together to produce a final image of the whole volume of interest. Such an approach is typically challenged by the "stitching" artifact issue wherein resulting final images often suffer from distinctive artifacts at the boundaries of the "stitched" pieces.

Existing techniques achieve correct combination of regional images through full spatial encoding along patient table motion direction. With other existing methods, the patient table is held stationary while data is collected and moved between the collection of the regional images. These techniques minimize "stitching" artifacts by using slab selection profiles that are as rectangular as possible, and/or discarding image data near the boundaries. As a result, these techniques tend to be inflexible, require prolonged radio frequency (RF) excitation, and involve considerable acquisition efficiency degradation.

What is needed is a method and system for extended volume imaging, such as head-to-toe imaging, using a MRI system in order to benefit from the specificity and image sensitivity of a MRI system. What is further needed is a method and system that is sufficiently fast to minimize image artifacts caused by patient motion.

SUMMARY OF INVENTION

In a first aspect, an imaging apparatus for producing Magnetic Resonance (MR) images of a subject is provided. The apparatus comprises a magnet assembly for producing a static magnetic field, a gradient coil assembly for generating a magnetic field gradient for use in producing MR images and at least one radiofrequency (rf) coil assembly for transmitting a radiofrequency pulse and for detecting a plurality of magnetic resonance (MR) signals induced from the subject. The apparatus further comprises a positioning device for supporting the subject and for translating the subject into the magnet assembly and a plurality of receivers for receiving the plurality of MR signals. Each of the receivers is adapted to be adjusted in phase or frequency changes in response to translation of the positioning device.

In a second aspect, a method for producing an image from an extended volume of interest within a subject using a Magnetic Resonance Imaging (MRI) system where the extended volume of interest is larger than an imaging portion of a magnet within the MRI system is provided. The method comprises the steps of: translating the extended volume using a positioning device along an axis of the MRI system through the imaging portion of the magnet wherein the positioning device is translated continuously at a plurality of incremented positions along the axis; detecting a plurality of MR signals from at least one radiofrequency (RF) coil for a given field-of-view within the MRI system as the positioning device is translated; and, sending the plurality of MR signals to a plurality of receivers. Each of the receivers are configured to be adjusted in at least one of phase and frequency in response to the positioning device being translated. The method further comprises computing a plurality of respective sub-images corresponding to the plurality MR signals for each of the plurality of receivers and for the given field-of-view (FOV) at each of the incremented positions and combining the plurality of respective sub-images to form a composite image of the volume of interest.

BRIEF DESCRIPTION OF DRAWINGS

The features and advantages of the present invention will become apparent from the following detailed description of the invention when read with the accompanying drawings in which.

DETAILED DESCRIPTION

Figure 1:
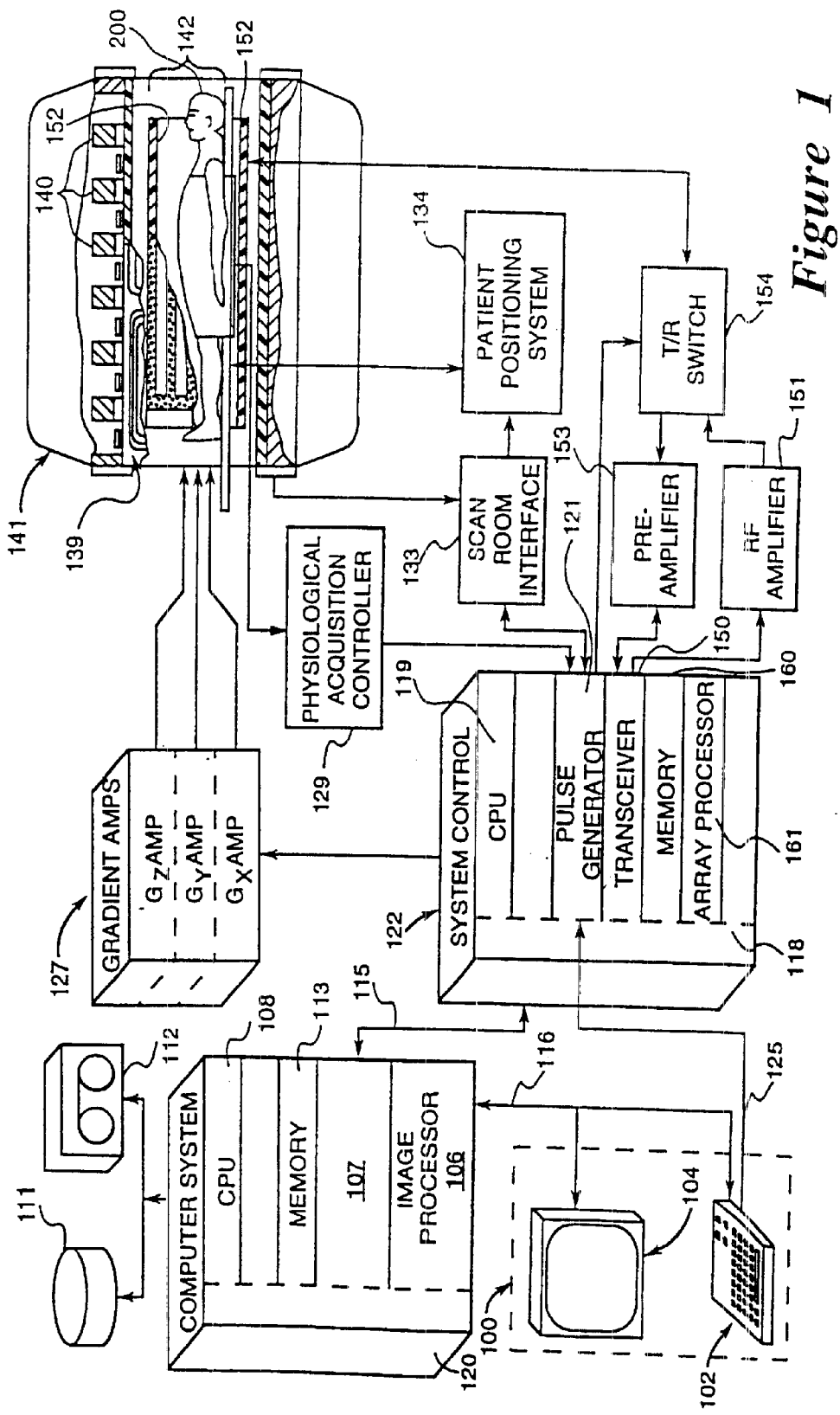
FIG. 1 illustrates a simplified block diagram of a Magnetic Resonance Imaging system to which embodiments of the present invention are useful.

FIG. 1 illustrates a simplified block diagram of a system for producing images in accordance with embodiments of the present invention. In an embodiment, the system is a MR imaging system which incorporates the present invention. The MR system could be, for example, a GE-Signa MR scanner available from GE Medical Systems, Inc., which is adapted to perform the method of the present invention, although other systems could be used as well.

The operation of the MR system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108, and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data that indicate the timing, strength, and shape of the radio frequency (RF) pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives subject data from a physiological acquisition controller 129 that receives signals from a number of different sensors connected to the subject 200, such as ECG signals from electrodes or respiratory signals from a bellows. And finally, the pulse generator module 121 connects to a scan room interface circuit 133 which receives signals from various sensors associated with the condition of the subject 200 and the magnet system. It is also through the scan room interface circuit 133 that a positioning device 134 receives commands to move the subject 200 to the desired position for the scan.

The gradient wave forms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. Volume 142 is shown as the area within magnet assembly 141 for receiving subject 200 and includes a patient bore. As used herein, the usable volume of a MRI scanner is defined generally as the volume within volume 142 that is a contiguous area inside the patient bore where homogeneity of main, gradient and RF fields are within known, acceptable ranges for imaging. A transceiver module 150 in the system control 122 produces pulses that are amplified by an RF amplifier 151 and coupled to the RF coil 152 by a transmit/receive switch 154. In an embodiment of the present invention, transceiver module 150 comprises a plurality of receivers that will be discussed in greater detail with reference to FIG. 2. The resulting signals radiated by the excited nuclei in the subject 200 may be sensed by the same RF coil 152 and coupled through the transmit/receive switch 154 to a preamplifier 153. The amplified MR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either a transmit or receive mode. It is to be appreciated that RF coil 152 is configured to be operable for MRI scanning as described below, in which a subject is translated on a positioning device along the z-axis. As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that is programmed to perform a sequel to provide an output in response to given input signals.

The MR signals picked up by the RF coil 152 are digitized by the transceiver module 150 and transferred to a memory module 160 in the system control 122.

When the scan is completed and an entire array of data has been acquired in the memory module 160, an array processor 161 operates to Fourier transform the data into an array of image data. These image data are conveyed through the serial link 115 to the computer system 107 where they are stored in the disk memory 111. In response to commands received from the operator console 100, these image data may be archived on the tape drive 112, or they may be further processed by the image processor 106 and conveyed to the operator console 100 and presented on the display 104. As will be discussed with reference to embodiments below, further processing is performed by the image processor 106 that includes reconstructing acquired MR image data according to embodiments described below.

Figure 2:
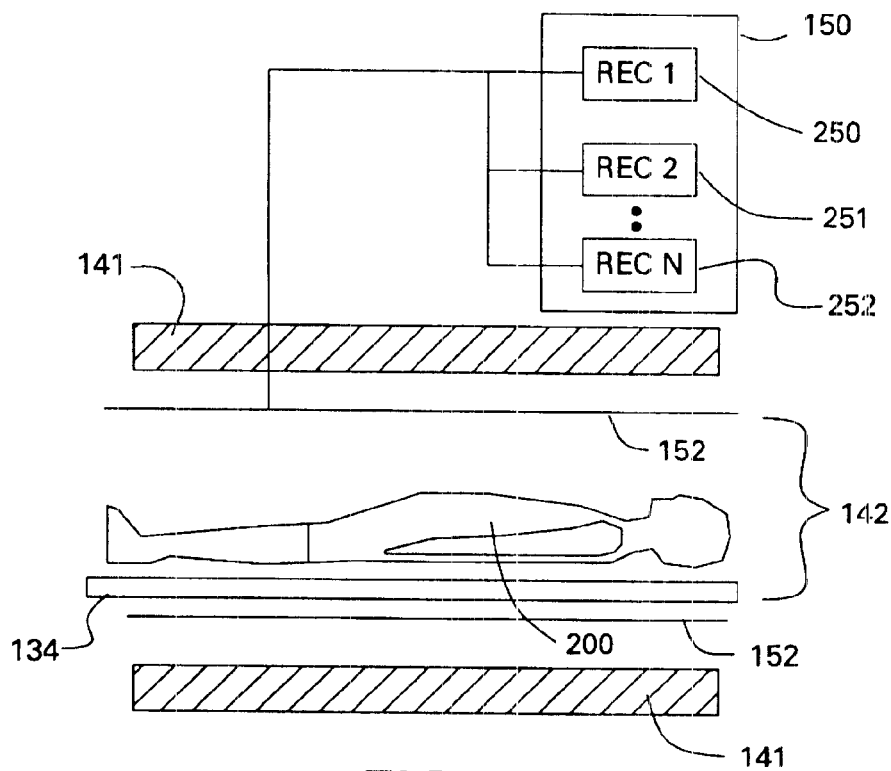
FIG. 2 is a side-view block diagram of a receiver arrangement for use in the MRI system of FIG. 1 and to which embodiments of the present invention are applicable; and, FIG. 3 is a simplified graphical illustration of a data acquisition sequence to which embodiments of the present invention are applicable.

Referring to FIG. 2, there is shown a side-view block diagram of a receiver arrangement for use in the MRI system of FIG. 1. As shown in FIG. 2, subject 200 is positioned on positioning device 134 of the MR scanner. As used herein, MR scanner refers generally to the MRI system. Subject 200 is translated through the useable volume (142 of FIG. 1) of the scanner at a constant rate until the entire body of the subject (or desired portion thereof) has passed through magnet assembly 141 (FIG. 1).

In an embodiment of the present invention, an imaging apparatus for producing Magnetic Resonance (MR) images of a subject is provided. The apparatus comprises a magnet assembly for producing a static magnetic field; a gradient coil assembly for generating a magnetic field gradient for use in producing MR images; at least one radiofrequency (rf) coil assembly for transmitting a radiofrequency pulse and for detecting a plurality of MR signals induced from the subject; a positioning device for supporting the subject and for translating the subject into the magnet assembly; and, a plurality of receivers for receiving the plurality of MR signals and being further adapted to be adjusted in phase or frequency changes in response to translation of the positioning device.

Multiple MR sub-images of portions of the subject are made while the subject is moved through the imaging portion of the MR imaging magnet. MR signals are detected from whole-body RF coil 152 (e.g. a body coil) and simultaneously sent to a plurality, N, of receivers which are shown as 250, 251 and 252 in FIG. 2. The description which follows corresponds to an exemplary embodiment in which N=2, and the receivers are receiver 250 and receiver 251. It is to be appreciated that further embodiments would comprise multiple receivers and image processing computations described below would be adapted by one skilled in the art for the selected number N of receivers. At the completion of subject's 200 movement through magnet assembly 141 (FIG. 1) the sub-images are processed by image processor 106 (FIG. 1) and combined to form a composite image of the entire subject.

In an embodiment of the receivers, the receivers are configured to be adjusted in phase or frequency in response to phase or frequency changes due to translation of the positioning device. During scanning either the phase or the frequency of the receivers (or transmitter) is continuously changed to match the phase and frequency changes of spin magnetization caused by patient motion through the geometrically-fixed gradient system of the magnet.

If it is desirable for the frequency-encoding direction to be parallel to the axis of subject motion, then it is the receiver frequency that is changed at a rate commensurate with the rate of translation of the positioning device (hereinafter "table motion"). The rate of frequency change can be determined from the table motion rate (in cm/sec), the gyromagnetic ratio of the nuclear spins (approx. 4250 Hz/Gauss for 1 H) and the scan rate (TR) (in ms). The table speed can be assumed to be slow during the short periods during data acquisition itself (typically 4–8 ms). In further embodiments, however, the receiver frequency is varied during data acquisition. If the frequency direction is chosen to be parallel to the table motion, then the optimal field-of-view (FOV) for the frequency-encoding direction will be the size of the RF coil divided by N.

If the operator desires that the phase-encoding direction of the image acquisition be parallel to the direction of table motion, then the receiver phase is changed as a function of an incremented position of the positioning device (hereinafter "table position"). In this case the optimal FOV of the phase-encoding direction of each sub-image would be twice the size of the RF coil to prevent phase-wrap artifacts.

If it is desirable for the slice-selection direction of the image to be parallel to the table motion (as in an axial slice), then the transmitter frequency is changed to cause the excitation slice to move through the magnet at the same rate that the subject moves. In this case there are no practical restrictions on the FOV of the sub-image.

It should also be noted that oblique scanning is possible by performing simple matrix rotations to the gradient subsystem and to the receiver and transmitters frequencies in a manner well known to those skilled in the art.

In the current embodiment of the present invention, an additional phase or frequency offset is added to each receiver causing the reconstructed data to be shifted by a distance corresponding to the field-of-view divided by N. In a exemplary embodiment of the invention in which the frequency-encoding axis of each sub-image is parallel to the table motion, the acquisition of a single sub-image is complete in 1/Nth the time it takes the subject to traverse the sensitive imaging volume of the magnet. Furthermore, the order of data acquisition can be modified so that k-space is traversed twice during the acquisition of each sub-image (e.g. odd numbered rows in the first half of the sub-image scan, even numbered rows in the second half). This aspect of the invention will be described in greater detail below and with reference to FIG. 3.

Once a sub-image is collected the phase or frequency of the receiver is reset, and a subsequent sub-image at an adjacent location within the subject is acquired. The process is repeated until the subject's entire body has passed through the magnet and has been imaged.

Because each receiver operates at a different phase or frequency, images acquired with each receiver will contain signals from different portions of the body. The fields-of-view of each receiver overlap each other, however because the relative offsets are FOV/N. Consequently, every part of the subject's body is acquired in a central portion of one sub-image.

In the exemplary embodiment of the invention, N=2 and 256 lines of k-space are acquired with the frequency direction of the acquisition applied in the direction of table motion. The frequency of both receivers is changed at a rate that causes image acquisition to be performed at the same anatomical location during the acquisition of a sub-image. Furthermore, the sub-images acquired with the two receivers are offset from one another by ½ the field-of-view.

With this embodiment the sequence of data acquisition is as follows:

| Receiver 1 | | Receiver 2 | |
| --- | --- | --- | --- |
| Sub image # | k-space | Sub image # | k-space |
| 1 | odd | — | — |
| 1 | even | 1.5 | even |
| 2 | odd | 1.5 | odd |
| 2 | even | 2.5 | even |
| 3 | odd | 2.5 | odd |
| 3 | even | 3.5 | even |

Figure 3:
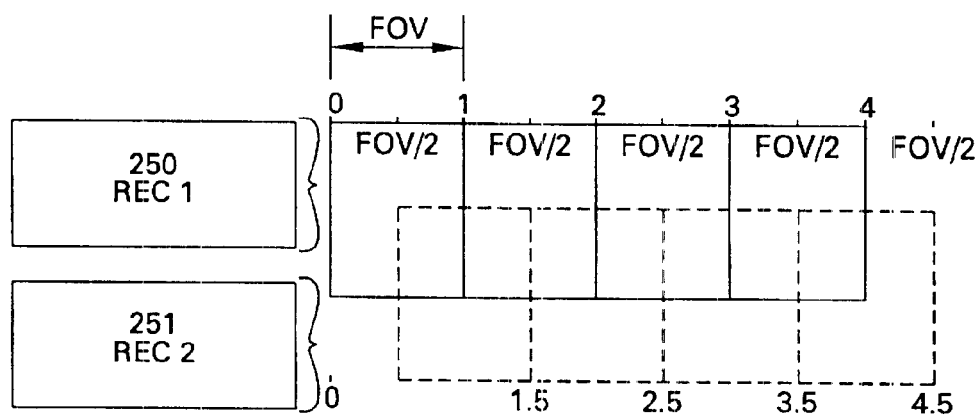

. . . and so on until the entire subject has been imaged.

illustrative embodiment which is shown in FIG. 3, the sub-image number represents both the time sequence and the relative location of the sub-image in the context of the subject's anatomy.

Note that the same RF pulses and magnetic field gradient pulses are used to simultanously generate data from the subject for both receivers. Because there are N=2 passes through k-space, the pulses used to acquire the second half of sub-image 1 are also used to acquire the first half of sub-image 1.5.

Once all the data has been acquired, an MR image of the entire body is created by combining the central portions of each sub-image. Since each receiver operates at a unique offset, every portion of the subject is imaged in a central portion of a sub-image and discontinuity artifacts associated with image edge boundaries ("stitching artifacts") are avoided.

In an alternate embodiment of the invention, the final composite image is created by combining full sub-images to obtain a composite image with an enhanced signal-to-noise ratio. In this embodiment, each point in the subject's anatomy is found in N sub images. Since these N images have only partially correlated noise, combining the full images will provide a signal-to-noise enhancement. For N=2, the noise in each sub-image is ½ correlated since ½ of the data in each sub-image is identical. Thus, the expected SNR gain would be sqrt(3/2) since the data acquired is equivalent to a 1.5 NEX acquisition. Conversely, if N=3, then the expected SNR gain would be sqrt (5/3) or equivalent to a NEX=5/3 acquisition. In general the SNR gain for using N receivers is given by the expression:

$$\mathrm{Sqrt}((2N-1)/N).$$

As N becomes large, the SNR gain approaches sqrt(2) or that of a NEX=2 acquisition (i.e. the SNR gain of imaging twice as long).

A further alternate embodiment of the invention employs a single receiver that is operated with the frequency direction applied parallel to the table motion. In this alternate embodiment the field-of-view of the receiver is set to be equal to the imaging volume of the magnet. At the beginning of the scan the center of the sub-image is set to be ¼$^{th}$ of the way into the active volume of the imaging system. Sub-images are collected over a period of time that corresponds to the time it takes a selected portion of anatomy to traverse ½ of the active imaging volume. Thus at the end of the acquisition of a sub-image, the center of the sub-image is $\frac{3}{4}^{th}$ of the way into the active volume of the imaging system. Upon the completion of the sub-image the next sub-image is initiated with an offset equal to ½ the FOV. Once all the sub-images have been collected the central portion of each sub-image is extracted and combined with other central portions to form the composite image. As with the prior embodiment extraction of the central portions of the image reduces the severity of "stitching" artifacts.

In another further embodiment, a single receiver is employed wherein the receiver is adapted to receive the plurality of MR signals from rf coil 152 and is further adapted to be adjusted in at least one of phase and frequency in response to translation the positioning device through the magnet assembly. In this embodiment, the receiver is also further adapted to collect image data for a field-of-view corresponding to a useable volume of the magnet assembly. Thereafter, processing of the MR signals is performed to compute a plurality of respective sub-images for the field-of-view (FOV) at each of a plurality of incremented positions as the subject is translated. A central portion of each of the plurality of respective sub-images is combined to form a composite image of the volume of interest.

Embodiments of the present invention provide for a MRI system that may be employed as a whole body screening tool for metastatic cancer and other diseases. In the embodiments for the methods of extended volume imaging, any MR pulse sequence (e.g. spin echo, fast spin echo, echo-planar, gradient echo, FIESTA or FISP, two-dimensional, three-dimensional and multi-slice) may be employed. Use of any MR pulse sequence is possible since only the phase or the frequency of the receiver is modified during a scan. Embodiments of the methods of the present invention allow the user to select the desired direction of the phase and frequency encoding directions in order to advantageously place phase-encoding artifacts in desired directions. The user is also able to select interleaved acquisition of multiple slices, if necessary.

In further embodiments, embodiments of the present invention are implemented as a hardware subsystem in the scanner that is independent of the pulse sequence itself. That way any pre-existing imaging strategy and information content can be obtained over the entire subject. A hardware system implementation would comprise incorporating a subsystem in the scanner that varies the receiver offset frequency or phase in response to changes in table position, or alternatively, changes the table position in response to changes in receiver frequency/phase.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. An imaging apparatus for producing Magnetic Resonance (MR) images of a subject, the apparatus comprising:
   a magnet assembly for producing a static magnetic field;
   a gradient coil assembly for generating a magnetic field gradient for use in producing MR images;
   at least one radiofrequency (rf) coil assembly for transmitting a radiofrequency pulse and for detecting a plurality of magnetic resonance (MR) signals induced from the subject;
   a positioning device for supporting the subject and for translating the subject into the magnet assembly; and,
   a plurality of receivers for receiving the plurality of MR signals, the receivers each being adapted to be adjusted in frequency in response to translation of the positioning device, wherein the plurality of receivers are configured to be adjusted in response to frequency changes due to translation of the positioning device.

2. The apparatus of claim 1 further comprising:
   an image processor for computing a plurality of respective sub-images corresponding to a field-of-view at a plurality of incremented positions of the positioning device and wherein the image processor is further adapted to combine the plurality of respective sub-images to form a composite image of the subject.

3. The apparatus of claim 2, wherein each of the receivers are offset from one another and the respective sub-images overlap.

4. The apparatus of claim 1, wherein the frequency is changed at a rate commensurate with a rate of translation of the positioning device.

5. The apparatus of claim 1 wherein the rf pulse is obtained from at least one of spin echo, fast spin echo, echo-planar, gradient echo, FIESTA or FISP, two-dimensional, three-dimensional and multi-slice pulse sequences.

6. A method for producing an image from an extended volume of interest within a subject using a Magnetic Resonance Imaging (MRI) system where the extended volume of interest is larger than an imaging portion of a magnet within the MRI system, the method comprising:
   translating the volume using a positioning device along an axis of the MRI system and the imaging portion of the magnet, the positioning device being translated at a plurality of incremented positions along the axis;
   detecting a plurality of MR signals from at least one radiofrequency (RF) coil for a given field-of-view within the MRI system as the positioning device is translated;
   sending the plurality of MR signals to a plurality of receivers, the receivers being configured to be adjusted in frequency in response to the positioning device being translated, wherein the receivers are adapted to be adjusted in frequency at a rate commensurate with a rate of translation of the positioning device;
   computing a plurality of respective sub-images corresponding to the plurality of MR signals for each of the plurality of receivers and for the given field-of-view (FOV) at each of the incremented positions; and,
   combining the plurality of respective sub-images to form a composite image of the volume of interest.

7. The method of claim 6 wherein the translating step is repeated until a selected length of the subject has been translated during the imaging portion of the magnet.

8. The method of claim 6 wherein each of the plurality of receivers is adjusted by an additional offset corresponding to FOV/N, where FOV is the field-of-view and N is a number of receivers.

9. The method of claim 8 wherein the combining step further comprises combining a central portion of each sub-image to form the composite image.

10. A method for imaging an extended volume of interest within a subject using a Magnetic Resonance Imaging (MRI) system comprising:

translating the subject using a positioing device into an imaging portion of a magnet assembly of the MRI system;

detecting a plurality of MR signals from a radiofrequency (RF) coil; and, sending the plurality of MR signals to a plurality of receivers, wherein the receivers are adapted to be adjusted in frequency in response to translation of the positioning device through the magnet assembly and wherein the receivers are adapted to be adjusted in frequency at a rate commensurate with a rate of translation of the positioning device and further adjusting the frequency of each receiver by a measure corresponding to a field-of-view divided by N, a number of receivers.

11. The method of claim 10 further comprising:

computing a plurality of respective sub-images corresponding to the plurality MR signals for each of the plurality of receivers and for the given field-of-view (FOV) at each of a plurality of incremented positions as the subject is translated; and, combining the plurality of respective sub-images to form a composite image of the volume of interest.

12. A method for imaging an extended volume of interest within a subject using a Magnetic Resonance Imaging (MRI) system comprising:

translating the subject using a positioning device into an imaging portion of a magnet assembly of the MRI system;

detecting a plurality of MR signals from a radiofrequency (RF) coil; and, sending the plurality of MR signals to a receiver, wherein the receiver is adapted to be adjusted in frequency in response to translation of the positioning device through the magnet assembly wherein the receivers are adapted to be adjusted in frequency at a rate commensurate with a rate of translation of the positioning device and further adapted to collect image data for a field-of-view corresponding to a useable volume of the magnet assembly;

processing the MR signals to compute a plurality of respective sub-images for the field-of-view (FOV) at each of a plurality of incremented positions as the subject is translated; and, combining a central portion or each of the plurality of respective sub-images to form a composite image of the volume of interest.

* * * * *